United States Patent

Kelleher et al.

[11] Patent Number: 5,876,438
[45] Date of Patent: Mar. 2, 1999

[54] POLYMERIC DEVICE FOR THE DELIVERY OF IMMUNOTOXINS FOR THE PREVENTION OF SECONDARY CATARACT

[75] Inventors: Peter J. Kelleher; Dominic M. K. Lam, both of The Woodlands, Tex.; Maureen P. Tarsio, Manlius, N.Y.

[73] Assignee: Houston Biotechnology Incorporated, The Woodlands, Tex.

[21] Appl. No.: 591,593

[22] PCT Filed: Aug. 2, 1993

[86] PCT No.: PCT/US93/07292

§ 371 Date: May 3, 1996

§ 102(e) Date: May 3, 1996

[87] PCT Pub. No.: WO95/03783

PCT Pub. Date: Feb. 9, 1995

[51] Int. Cl.[6] .................................................... A61F 2/14
[52] U.S. Cl. ............................................................ 623/4
[58] Field of Search ................................................ 623/4–6

[56] References Cited

U.S. PATENT DOCUMENTS

| | | | |
|---|---|---|---|
| 3,416,530 | 12/1968 | Ness | 128/261 |
| 4,128,318 | 12/1978 | Sieglaff et al. | 351/160 |
| 4,170,043 | 10/1979 | Knight et al. | 623/6 |
| 4,240,163 | 12/1980 | Galin | 623/6 |
| 4,432,751 | 2/1984 | Emery et al. | 604/49 |
| 4,449,983 | 5/1984 | Cortese et al. | 604/892 |
| 4,526,938 | 7/1985 | Churchill et al. | 525/415 |
| 4,664,911 | 5/1987 | Uhr et al. | 424/85 |
| 4,671,954 | 6/1987 | Goldberg et al. | 424/450 |
| 4,725,428 | 2/1988 | Miyahara et al. | 424/50 |
| 4,745,160 | 5/1988 | Churchill et al. | 525/415 |
| 4,766,106 | 8/1988 | Katre et al. | 514/12 |
| 4,853,224 | 8/1989 | Wong | 424/427 |
| 4,863,457 | 9/1989 | Lee | 424/428 |
| 4,871,350 | 10/1989 | Lam et al. | 604/49 |
| 4,871,716 | 10/1989 | Longo et al. | 514/2 |
| 4,917,888 | 4/1990 | Katre et al. | 424/85.91 |
| 4,918,165 | 4/1990 | Soll et al. | 424/427 |
| 4,966,577 | 10/1990 | Crosson et al. | 604/420 |
| 4,997,657 | 3/1991 | Wong | 424/428 |
| 5,098,443 | 3/1992 | Parel et al. | 623/4 |
| 5,378,475 | 1/1995 | Smith | 424/473 |

FOREIGN PATENT DOCUMENTS

| | | | |
|---|---|---|---|
| 0267005 | 5/1988 | European Pat. Off. | A61K 37/02 |
| 0299467A1 | 1/1989 | European Pat. Off. | A61K 47/00 |

OTHER PUBLICATIONS

Marsh, *J. Biol. Chem.*, (1989) 264:10405–10410.
Langer & Folkham, *Nature*, (1976) 263:797–799.

Primary Examiner—David J. Isabella
Assistant Examiner—John M. Black
Attorney, Agent, or Firm—Lahive & Cockfield, LLP; Jane E. Remillard; Megan E. Williams

[57] ABSTRACT

Intraocular devices together with methods for their preparation and use are provided, which are capable of sustained release of an antiproliferative agent, particularly an immunotoxin comprising a cytotoxic moiety. The intraocular devices are implanted in the eye where the immunotoxin is released from the intraocular device. The device may be used to inhibit proliferation of remnant lens epithelial cells, particularly after extracapsular cataract extractinon. The components of the device can be provided as kits, but preferably are provided in a form suitable for use with an IOL or coated onto an IOL.

12 Claims, 3 Drawing Sheets

Immunotoxin-polymer Solution + IOL = Immunotoxin-coated IOL

Immunotoxin-
polymer Solution     IOL     Immunotoxin-
                             coated IOL

FIGURE 1

Side view

IOL with associated polymer matrix

IOL with immunotoxin absorbed into matrix

Immunotoxin Solution

Face view

FIGURE 2

POLYMERIC DEVICE FOR THE DELIVERY OF IMMUNOTOXINS FOR THE PREVENTION OF SECONDARY CATARACT

FIELD OF THE INVENTION

This invention relates to an intraocular polymeric device and methods for its preparation and use, wherein the polymeric device comprises a polymer and at least one cytotoxic agent, particularly an immunotoxin for prevention and treatment of secondary cataracts.

BACKGROUND

An intact posterior lens capsule is required for implantation of a wide variety of intraocular lenses. A surgical technique that preserves the posterior lens capsule, and which has found use in the treatment of cataracts, is generically termed extracapsular cataract extraction. The technique includes extracapsular cataract extraction, phacoemulsification, endocapsular extraction and intercapsular extraction. Newer methods of extracapsular cataract extraction under development, such as the Kelman phaco fly, would remove a cataract through a puncture of the lens capsule and refill the lens capsule bag with a flexible substance or an inflatable lens to restore vision and to preserve or restore natural accommodation.

Extracapsular cataract extraction is a desirable method for removing cataracts due to a lower incidence of postoperative complications such as cystoid macular edema and possible retinal detachment. However, this surgical method is accompanied by a significant incidence of posterior lens capsule opacification, which may require additional surgical procedures such as posterior capsulotomy or repolishing of the posterior lens capsule to provide good vision. Virtually all pediatric patients and approximately 50% of adult patients undergoing extracapsular cataract extraction develop an opaque secondary cataract within 3 to 5 years.

The pathogenesis of posterior lens capsule opacification after extracapsular cataract extraction is reported to be due to proliferation of remnant lens epithelial cells on the posterior lens capsule to form abortive lens "fibers" and "bladder" cells (i.e., Elschnig's pearls). Various cytotoxic agents are reported to inhibit this secondary cataract formation or posterior lens capsule opacification, including vincristine and vinblastine. Radiation has also been tried and was reported to be promising. Methotrexate and retinoic acid have been reported for instillation in the anterior chamber of the eye to kill residual lens epithelial cells and thus prevent posterior lens capsule opacification. These methods are relatively non-specific and can damage and/or kill other cells in addition to the lens epithelial cells.

Techniques which are designed to more specifically kill lens epithelial cells have included introduction of immunotoxins capable of binding specifically to residual lens epithelial cells on the lens capsule remnant at the time of cataract surgery. These immunotoxins have been shown to inhibit proliferation of lens epithelial cells in vitro. However, the immunotoxin activity is both dose and time dependent and it is difficult to maintain the immunotoxin in the posterior chamber at a concentration and for a time sufficient to prevent proliferation of and/or to kill the residual lens epithelial cells. The immunotoxin passes through the pupil into the anterior chamber where it is lost through normal aqueous outflow. It would therefore be of interest to develop methods and compositions for retarding loss of the immunotoxin from the posterior chamber for use in preventing secondary cataract formation or posterior lens capsule opacification. Such a device would have the advantage of providing a sufficient concentration of immunotoxin in the vicinity of the eye for a time sufficient to kill any lens epithelial cells remaining in the eye after extracapsular extraction.

Relevant Literature

Biodegradable microcapsules for use in the eye are disclosed in Wang (U.S. Pat. No. 4,853,224). An eyeball medication dispensing tablet has been disclosed in U.S. Pat. No. 3,416,530. U.S. Pat. No. 4,526,938 discloses copolymers which can be used to provide for continuous release of polypeptides. See also Heyrman, et al., (1989) *J. Cataract Refract. Surg.*, 15:169–175.

Examples of polymeric delivery systems include Sherwood, et al. (1992) *Bio/Technology* 10:1446–1449; Hora, et al. (1990) *Bio/Technology* 8:755–757.

Immunotoxins and their use for treating secondary cataracts are described in U.S. Pat. Nos. 4,871,350 and 4,432,751 and European Patent 0088606. U.S. Pat. No. 4,432,751 also discloses use of a combination of monoclonal antibodies and complement for preventing secondary cataracts. Complement-fixing monoclonal antibodies which bind specifically with lens epithelial cells and have low or no cross-reactivity with other cells found in the anterior segment of the eye are disclosed in U.S. Pat. No. 5,202,252. The use of sugars such as trehalose to prepare antibodies for storage is described in Rowser (U.S. Pat. No. 4,891,319).

SUMMARY OF THE INVENTION

A novel intraocular device, together with methods of preparation and use, is provided for treatment and/or prevention of secondary cataracts. The device comprises a biologically inert polymer and at least one cytotoxic agent, particularly an immunotoxin, capable of binding specifically to lens epithelial cells. The cytotoxic agent is associated reversibly with the polymer so as to provide for sustained delivery of the cytotoxic agent following implantation of the device into the eye. The intraocular device is prepared in several ways including by immersing a polymer matrix in a solution of a cytotoxic agent whereby the cytotoxic agent is pulled into the matrix by capillary action, by mixing the cytotoxic agent with the polymer prior to association with a support, such as an intraocular lens (IOL), or by coating a polymer matrix bound covalently or non-covalently to a support, such as an IOL, with the cytotoxic agent. In use, the intraocular device is introduced into the anterior or posterior chamber of the eye during or following cataract surgery. The cytotoxic agent is continuously released from the intraocular device in the vicinity of the posterior chamber at a concentration and for a time sufficient to kill any residual lens epithelial cells thus preventing the formation of secondary cataracts.

BRIEF DESCRIPTION OF THE DRAWINGS

FIG. 1 shows preparation of an immunotoxin coated IOL starting from a mixture of immunotoxin and polymer in solution.

FIG. 2 shows preparation of an immunotoxin coated IOL using a two-step procedure: The polymer is first coated onto the IOL, which is then interacted with the immunotoxin solution. Upper view is IOL "edge" view; the intraocular device covers essentially the entire IOL surface. Lower view is IOL "face" view; the intraocular device essentially is a ring around the IOL.

DESCRIPTION OF THE SPECIFIC EMBODIMENTS

Figure 3:
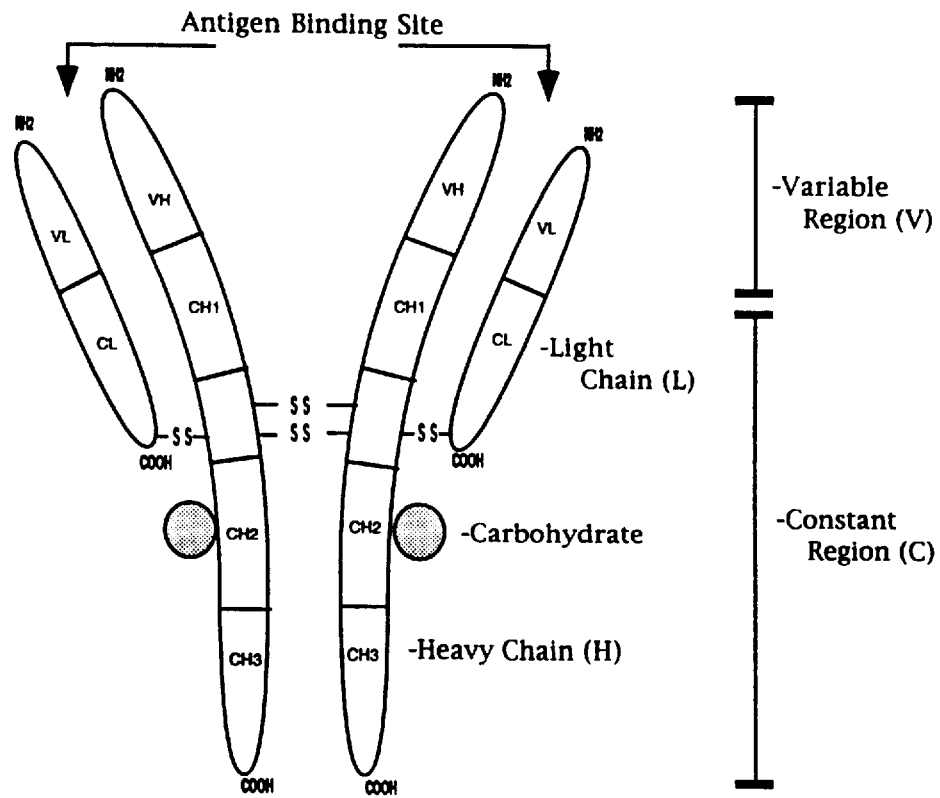
FIG. 3 shows the structure of a typical IgG antibody.

The present invention relates to intraocular devices for preventing and/or treating secondary cataracts, particularly at the time of or following extracapsular extraction. "Preventing secondary cataracts" is intended to mean preventing growth of any residual lens epithelial cells on the lens capsule remnant after removal of a primary cataract by killing any residual lens epithelial cells present in the eye. The primary cataract can be of any type, including senile, juvenile and radiation-induced. "Treating secondary cataract" is intended to mean use of the device to inhibit proliferation of, preferably to kill, lens epithelial cells which have grown across the optic axis of the posterior lens capsule following removal of the primary cataract.

Treating and/or preventing secondary cataract relies on the introduction of an intraocular device into the posterior or anterior chamber of the eye, wherein the intraocular device comprises a polymer or macromolecule and at least one cytotoxic agent capable of selectively inhibiting proliferation of and/or killing any remnant lens epithelial cells present in the posterior chamber. The cytotoxic agent is dispersed in the macromolecule, particularly reversibly associated to or physically entrapped in the polymer, where the polymer optionally is cross-linked to form a matrix as a means of decreasing the rate of release of the cytotoxic agent from association with the macromolecule. In use, the device thus limits diffusion of the cytotoxic agent both temporally and spatially. The purpose of the described invention is to prolong the exposure time of any remnant of lens epithelial cells present in the posterior chamber to therapeutic concentrations of cytotoxic agent.

The intraocular device may be provided in several forms. It may be provided as a stand-alone device which can be used alone or in conjunction with other devices such as IOLs. It may be provided coated onto a support. It may be provided as components for bonding onto a support, for example, an IOL. Where the polymer itself is rigid enough to act as its own support, for example, crystalline, rubbery PEO-based hydrogels that are mechanically strong but not brittle, the polymer may be cast into a form for use, in conjunction with an IOL, where the form of the intraocular device is, for example, a circular ("O") ring or a donut capable of fitting around an IOL or to fit in the lens capsule with an IOL. The device is prepared having the diameter of the lens. It is then be placed in the eye so as to go around the periphery of the capsule. After the device is in place, an IOL can then be inserted.

Semi-rigid to flexible polymers which are degradable by water, such as polyglycolic acid, polygalactin or polyglyconate may be used for preparing support structures such as O-rings. Once the structures are formed, they then may be treated or coated with the intraocular device, where the polymer of the device may be the same or different from the polymer used to prepare the desired structure. Where the polymeric device is coated onto an IOL, generally it is coated onto the entire IOL, but more usually, the polymeric device is coated onto the haptic portion or supporting loops of the IOL. Generally the IOL support is prepared from polymers such as polymethylmethacrylate or silicone.

Various macromolecules may be used for preparing the intraocular device. Water soluble polymers may be used which may be mixed directly with the cytotoxic agent in solution. The water soluble polymers may also be treated with cross-linking agents prior to interaction with a cytotoxic agent. Water insoluble polymers may also find use, where the polymer may be hydrated in a solution of the cytotoxic agent.

The characteristics of the polymer will include the following. The polymer must be biologically inert and physiologically compatible with tissues in the eye, i.e., it must be a polymer which does not in and of itself induce an inflammatory response or affects the viability of cells in the eye tissue beyond that occurring as a result of the surgical procedure. For some applications it may be desirable to use a biodegradable polymer, i.e., one which is subject to hydrolysis or which is broken down by biochemical processes such as enzymatic action. Examples of such polymers are the polymers used in dissolving sutures, for example, polyglycolic acid, collagen and the like.

One of the aims of this invention is to provide a means for sustained release from the device of a cytotoxic agent in the posterior chamber of the eye, therefore the polymer should be one which provides for reversible association of the cytotoxic agent with the polymer. Polymers which provide this characteristic include those capable of forming matrices so as to physically entrap the cytotoxic agent. Such a polymer may additionally be able to be cross-linked so as to provide a matrix of varying porosity. By varying the porosity, the rate of diffusion of the cytotoxic agent may be varied. The polymer should be hydrophilic so that when it is dry it has the capacity to take up water and cytotoxic agent so as to form a hydrogel which finds particular use in those cases where the polymer is to be formed (cast) prior to interaction with the cytotoxic agent. Generally, the polymer must not inactivate or react with the cytotoxic agent, although in some applications, a weak electrostatic charge on the polymer may be useful for reversibly binding the cytotoxic agent to the polymer. Examples of compounds which may form gels upon hydration include sodium hyaluronate and chondroitin sulfate.

The polymeric device may be prepared in several ways depending upon the intended form and the particular polymer to be used, as well as the nature of the cytotoxic agent, e.g. whether it is a small molecule or a large molecule, and the best way to reverably associate the agent with the polymer. For example, where the polymer is an insoluble polymer the cytotoxic agent can be associated with a polymer by hydrating the polymer in a solution of the cytotoxic agent. The resulting hydrated polymer may take, for example, the form of a gel or a more rigid form. Examples of such hydrophilic polymers include cross-linked polyethylene oxide (PEO) and other polymers cross-linked with multifunctional alcohols (polyethylene glycols) and diisocyanates.

Where it is desired to provide the intraocular device with a support, particularly where the combination of the polymer and the cytotoxic agent has insufficient rigidity to cast into a form suitable for use in the eye, the polymer, particularly dry polymer, may be mixed with the cytotoxic agent and coated onto a support material. The support material may be any material which is biocompatible with tissues in the eye such as, for example, a ring of collagen or polyglycolic acid for use with an IOL, or the intraocular device may be coated directly onto an IOL. Providing the intraocular device either in a stand-alone form or coated onto an existing support offers the advantage that the intraocular device may be used with existing prototypes of IOL.

The polymer in a water soluble intraocular device, such as a hydrogel, can use an IOL as a support, where the device is applied as a coating to the IOL. The coating may be applied in a single step as described above, where the polymer and the cytotoxic agent are mixed prior to coating onto the IOL. Alternatively, the polymer may be bound either covalently or noncovalently to an IOL. The IOL with the polymer attached can then be dipped into a solution of the cytotoxic agent, which may then be dried and stored until implantation in the eye, or used immediately for implantation. Particularly where the polymer is to be adhered to the IOL prior to interaction with the cytotoxic agent, the polymer may as necessary be altered chemically, so that it may be reacted directly with the surface of the IOL to form covalent bonds to the IOL.

The choice of a particular macromolecule will depend at least in part on the method of use of the intraocular device and its physical form. Thus, where the intraocular device is to be used in conjunction with an IOL and has to be cast into a particular form, it will be desirable to use a polymer which is capable of being cast into the desired form. Examples of such polymers include polymers capable of forming hydrogels and structural proteins such as collagen which can be cross-linked to form a rigid structure. Where the intraocular device comprises a coating to be applied to an IOL, the polymer is desirably one which will not affect the optical properties of the IOL. Another desirable property of the polymer for some applications is the capability of adhering to the surface of an IOL.

The preferred characteristics of the polymer include capacity for noncovalently interacting with or entrapping the cytotoxic agent. This capability provides for a source of cytotoxic agent in the eye which is released slowly into the eye and which thereby serves to decrease degradation of the immunotoxin which may occur from exposure to fluids in the eye or to decrease the removal by normal ocular processes of the cytotoxic agent from the eye. The polymer may be soluble or insoluble and will be capable of adsorbing the cytotoxic agent either chemically, e.g., by way of electrostatic charge, or physically, e.g., by capillary action and/or entrapment, without affecting its therapeutic properties, while serving to retain the cytotoxic agent at the site of introduction. The polymer may be a proteinaceous material that is physiologically acceptable to the internal environment of the eye of the host, generally a human. The proteinaceous material may be an individual peptide, but generally is a combination of peptides or proteins, e.g., albumin or other proteins, or structural proteins such as collagen, where the protein or polypeptide is crosslinked to provide for the desired matrix structure.

Where proteinaceous, particularly collagenous, material is used for preparing the intraocular device, it may be derived from any mammalian host source, such as bovine, porcine or human, or may be prepared, as available, by other techniques, e.g., recombinant DNA techniques. The collagen employed may be natural collagen or may be modified, such as tropocollagen, atropocollagen, or the like. The collagen may be nonimmunogenic, immunogenic, or only slightly immunogenic. Various methods for preparing collagen or derivatives thereof in purified form for administration to a mammalian host are known in the literature. These methods may be found in such patents as U.S. Pat. No. 3,949,073 and references cited therein. Of interest is bovine collagen which is purified and is obtained from young cows or calves. Purification will normally involve dispersion or precipitation from various media, e.g., dilute acetic acid.

In addition, the cytotoxic agents can be employed encapsulated in liposomes or other controlled rate release compositions, which are included in the polymeric material, so as to provide for separate and distinct rates of release of the cytotoxic agents. In this way, multiphasic compositions can be prepared, so as to provide for sustained release of the cytotoxic agent over long periods of time. Formation of liposomes with inclusion of various materials is described in Papahadjopoulos (1978) *Annals of the N.Y. Academy of Sciences,* 308; Gregoriadis and Allison (1980) *Liposomes in Biological Systems* (John Wiley and Sons); Leserman et al., *Nature* (1981) 293:226–228; Barhet et al., *Supramol. Struct. Cell Bio. Chem.* (1981) 16:243–258; and Heath et al., *Science* (1980) 255:8015–8018.

When used with cytotoxic agents lacking specificity for epithelial cells, the liposomes themselves could be retained in the eye by, for example, coupling the glycoprotein streptavidin to the liposome as a biochemical linker. See, for example, U.S. Pat. No. 4,885,172. Monoclonal antibodies or IgG capable of binding specifically to epithelial cells can be coupled to the streptavidin. Following introduction into the eye, the liposomes bind specifically to lens epithelial cells. Other methods of encapsulation also can be employed where the cytotoxic agent is encapsulated in a biodegradable coat and the rate of release is related to the thickness of the biodegradable coat.

The cytotoxic agent generally is a conjugate of a protein macromolecule capable of binding at least substantially specifically to epithelial cells, particularly lens epithelial cells, as compared to other cells which may be present in or in contact with the anterior or posterior chamber of the eye. For the most part, the cytotoxic compositions will be conjugates of a monoclonal antibody or its equivalent with a cytotoxic agent. However, where the monoclonal antibody or its equivalent has the capacity to fix complement, the monoclonal antibody alone may be used. The monoclonal antibody may be toxic by combination with either endogenous complement, or as appropriate complement may be injected subsequent to introduction of the monoclonal antibody into the anterior or posterior chamber of the eye.

The monoclonal antibody may be produced as a result of hybridoma formation and expression by the hybridoma, whether in culture or present as ascites, a monoclonal antibody fragment, such as Fab, $F(ab')_2$, Fv, a recombinant variable region, a T-cell receptor, or the like. The monoclonal antibodies and receptors may be any mammalian species, including murine, rabbit, human or the like, or combinations thereof, such as chimeric antibodies, having a human constant region and a mouse or other mammalian source variable region. The antibodies may be any class or subclass, such as IgA, IgD, IgG, IgM, and may include IgG1, 2a, 2b, or 3 or the human equivalents thereof. The monoclonal antibodies may be derived either from a simple hybridoma cell line or may be a mixture or "cocktail" of two or more monoclonal antibodies derived from different hybridoma cell lines, where the antibodies would bind to the same or different antigenic moieties as the epithelial cells.

The methods for preparing the monoclonal antibodies are well established as evidenced by the numerous references described above (see "Relevant Literature"). An animal is hyperimmunized with a suitable immunogen, with or without addition of adjuvant. Various epithelial cells may be used as the immunogen, particularly human epithelial cells, including tumor cells originating from epithelial cells, for example HeLa cells, although other species may find use, e.g., primates. Whole cells are preferred, however homogenates, membrane fragments or the like, can be used. The source of the cells includes cells in tissue culture, surgical specimens such as tissues removed during cataract surgery, biopsy specimens, and the like.

In accordance with the subject invention, a mammal, which can be a mouse or other small mammal, is hyperimmunized with the immunogen. Methods of immunization are well known and are amply described in the literature. The immunogenic material, generally about $10^5$ to about $10^6$ cells or cell equivalents, is injected with or without adjuvant into the mammal, or by repeated injections over relatively short periods of time. To ensure the hyperimmunization of the animal, 2–6 subsequent booster injections are administered. The animals are then killed, usually within 1–5 days after the last injection, when it has been determined that a suitable titer of antibody has been obtained. Antibody-producing cells such as spleen cells or lymphocytes from the immunized animal are removed and immortalized.

The method of cell fusion is not a critical portion of this invention and various techniques may be employed. Generally a nonanoic detergent, for example polyethyleneglycol (PEG), is used as the fusigen. The antibody-producing cells, for example spleen cells and myeloma cells are combined in the presence of a known ionic detergent conveniently PEG1540 and other additives, for example, serum-free Dulbeccos modified Eagle's medium (SF-DMEM) for approximately 5 minutes. The excess nonanoic detergent is then rapidly removed by washing the cells. The cells are promptly dispensed into small culture wells at a relatively low density, ranging from about $1 \times 10^5$/well to about $5 \times 10^5$/well in appropriate medium, commonly a selective medium comprising hypoxanthine, and aminopterin and thymidine (HAT) medium.

After a sufficient period, usually one to two weeks, colonies of hybrids are observed. The colonies are then screened for antibodies which bind at least substantially specifically to epithelial cells. Once colonies producing the desired antibodies have been identified, the colonies may be perpetuated to provide for a continual source of the desired antibodies.

To identify hybridomas of interest, antibodies secreted by the immortalized cells are screened to identify the clones that secrete antibodies of the desired specificity. Screening of the hybridoma clones may be by binding to epithelial cells, particularly lens epithelial cells, using an ELISA assay. Other screening methods include radioimmunoassay and immunohistochemical staining of cryostat sections of ocular tissue. Furthermore, the resulting monoclonal antibodies may be isolated and modified by truncating the constant region by various peptidase digestions. The monoclonal antibodies may be reduced to provide for Fab fragments with available mercaptan sites for conjugation to other compositions. T-cell receptors may be obtained as described in W085/03947.

To obtain hybridoma cell lines secreting monoclonal antibodies directed to a single antigenic determinant associated with epithelial cells, the hybridoma cells may be cloned using, for example, limiting dilution. The stage at which the cells may be cloned is not critical to the invention, and may be before identification of colonies secreting antibodies of interest, or later. However, to avoid overgrowth of antibody producing cells with non-antibody producing cells, the colonies are preferably cloned as soon after fusion as practicable.

For large-scale production of antibodies, the hybridomas may be introduced into the peritoneal cavity of a mouse or other mammal and grown as ascites tumors. Antibodies may then be isolated from the ascites fluid. Alternate methods for large-scale production of monoclonal antibodies including introducing subcutaneous tumors using the method described and collecting blood from the animal. The hybridoma cells can also be grown on a large-scale in tissue culture. Where the cells secrete the antibodies into the growth medium, the conditioned growth medium containing the antibodies can be collected for antibody isolation. Where the hybridoma cells do not secrete the antibodies, the cells may be collected, lysed using conventional means, and antibody purified from the cell lysate. Methods of purifying monoclonal antibodies are well known to those skilled in the art.

The binding compositions having specificity for epithelial cells, may be joined to a wide variety of toxic agents which may be derived from microorganism or plant sources of particular interest are the toxic subunits of naturally occurring toxins, such as ricin, abrin, diphtheria toxin, etc. See for example Oeltmann and Heath, *J. Biol. Chem.* (1979) 254:1022–1027; Yule and Neville Jr., *Proc. Natl. Acad. Sci. USA* (1980) 77:5483–5486; Gilliland et al., *Proc. Natl. Acad. Sci. USA* (1978) 75:5319–5323; U.S. Pat. No. 4,379, 145; GB2034324 and Masuho et al., *Biochem. Biophys. Res. Commun.* (1979) 90:320–326; and Blythman, *Nature* (1981) 290:145, the relevant disclosures of which are incorporated herein by reference.

Illustrative toxin A-chains or similarly effective moieties include diphtheria toxin A-chains, enzymatically active proteolytic fragments from *Pseudomonas aeruginosa* exotoxin-A, ricin A-chain, abrin A-chain, modeccin A-chain, and proteins found in various plants having similar activity, such as the plants *Gelonium multiflorum, Phytolacca americana, Croton tiglium, Jatropha curcas, Momordic charantia,* wheat germ, the toxin saponin from *Saponaria officinalis* (Thorpe et al., *J. Natl. Cancer Inst.* (1985) 75:151), Chinese cucumber toxin Trichosanthin (McGrath et al., *Proc Nat Acad Sci (USA)* (1989) 86:2844–2848). Of particular interest is ricin A-chain. Also, mutant species of the toxins of the species may be used, such as CRM45 (Boquet et al., *Proc. Natl. Acad. Sci. USA* (1976) 73:4449–4453).

The toxic agents and moiety providing for binding to the epithelial cells may be linked, usually by a bond which is cleavable cytoplasmically. Convenient linkages include disulfide, particularly where the toxic agent has an intrinsic sulfur, or other links, such as peptide links, urea links, thioethers, imines, amides, imides, amidines, etc. Functional groups which may find employment include carboxylic acid groups, amino groups, imines, aldehydes, isocyanates, mercaptans, olefins, or the like. In addition, more complex linking groups can be employed, where a group may be bound to one of the moieties in the conjugate to provide for convenient linkage to an intrinsic group of the other moiety. For example, the N-hydroxysuccinimide ester of m-maleimidoylbenzoic acid may be employed to prepare an amide of the toxin, which may then be linked through an available sulfur atom on the monoclonal antibody to provide a thioether.

Exemplary cytotoxic agents may have the following formula:

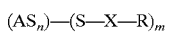

wherein:

$AS_n$ indicates the toxic agent having one or more sulfur groups as part of the agent; n is 1 or up to the number of sulfur groups present in the toxic agent which are present as available mercaptide groups, generally being up to about 4; R is a monoclonal antibody, T-cell receptor or derivative thereof; and m is 1 up to n, usually being from 1 to 2; and X is a linking group and may be a bond or a group of from about 1 to 20, usually 1 to 12 atoms other than hydrogen, which include carbon, nitrogen, oxygen and sulfur. Sulfur will normally be bonded to carbon, particularly aliphatically saturated. X may be aliphatic, alicyclic, aromatic, heterocyclic or combinations thereof, generally having from O to 6, more usually from about O to 4, preferably about 1 to 4 heteroatoms, wherein oxygen and sulfur are present as oxo or non-oxo-carbonyl or the thio analogs thereof, or ether (including thioether), and nitrogen is present as amino or amido. For the most part the heteroatoms will be bonded solely to carbon.

Illustrative groups linking the disulfide include aminoethylene 3-propanyl methylene carbonyl, α-succinimidyl, 3-propylenethiocarbonyl. The groups which may be used are for the most part conventional groups providing for a disulfide linkage. The disulfide compound is one which is capable of reacting with the cell-specific ligand, whereby a mercaptide group may be displaced from the disulfide, resulting in a new disulfide linkage between the toxic agent and the ligand.

For the most part, the linkages will be aliphatic of from about 1 to 6 carbon atoms, providing for an amide bond to the receptor, although this is primarily a matter of convenience, not necessary to the operability of the subject compositions.

The cytotoxic agent can be prepared as a fusion toxin by expression of a recombinant DNA sequence encoding the cytotoxic agent. The required recombinant DNA sequence is constructed by isolating a macromolecule having the desired target cell specificity (specificity domain) and ligating it to a protein toxin gene (cytotoxic gene).

The specificity domain and cytotoxic domain in general comprise portions of a single polypeptide chain. The fusion toxin chain may be represented by the formula:

$$\text{Sp-Jp-Ct} \quad (1)$$

where Sp indicates the specificity domain; Jp indicates at least one peptide bond, optionally including a peptide sequence, joining the specificity and cytotoxic domains; and Ct indicates the cytotoxic domain, i.e., the peptide backbone of the specificity domain is joined to the peptide backbone of the cytotoxic domain through Jp. In its simplest form, where Jp constitutes a single peptide bond, the fusion toxin by the following structure:

$$X—NH—CHR_N—CO—NH—CHR_1—CO—Y \quad (2)$$

where $X—NH—CHR_n—CO—$ is the C-terminal nth amino acid residue of domain X and $NH—CHR_1—CO—Y$ is the N-terminal 1st amino acid residue of domain Y. Alternatively, Jp can be a joining peptide of arbitrary sequence and length which joins the peptide backbones of the specificity and cytotoxic domains through the peptide backbone of Jp, with the C-terminus of Jp joined by a peptide bond to the N-terminus of domain Y and the N-terminus of Jp joined by a peptide bond to the C-terminus of domain X. Jp may be cleavable to allow release of the toxin from the specificity domain. In either case, the two domains are joined through at least one peptide bond to make a single polypeptide chain.

Although in many embodiments Sp comprises the N-terminal end of the polypeptide, analogous to the arrangement of natural antibodies, immunotoxins can be created with Ct at the N-terminus. The specificity and cytotoxic functions are mediated by independent domains which in general are little affected by the presence of the other. In rare cases in which a particular fusion toxin functions significantly less efficiently than the sum of the constituent domains, steric hindrance is the probable cause, and can be remedied by increasing the length of the Jp or by reversing the order of the domains.

Fusion toxins are prepared by expression of a recombinant DNA sequence encoding the polypeptide. The required recombinant DNA sequence may be constructed by the steps of: isolating cDNA encoding the light and heavy chain genes of the monoclonal antibody exhibiting the desired specificity for epithelial cells from the corresponding hybridoma; isolating cDNA encoding a desired protein toxin; isolating the appropriate fragment of DNA from the heavy and light chain genes; ligating the two $V_H$ and $V_L$ encoding fragments in the same orientation and in-frame through a DNA region encoding a joining peptide as described in the definition of Jp to form the specificity domain Sp; and ligating, in-frame, the gene encoding the toxin to the gene encoding the specificity domain, optionally through a DNA encoding a joining peptide described in the definition of Jp.

An expression vector comprising the ligated DNA is then constructed and used to transfect a host organism which is then grown to express the fusion toxin. If a secretory leader sequence has been provided in the expression construct, the fusion toxin can be isolated from the growth medium and purified. Alternatively, where secretion is not provided for, the cells can be lysed using methods known to those skilled in the art and purified so as to be substantially free of other cellular components.

In the first step for constructing the DNA sequence encoding the specificity domain, a monoclonal antibody capable of binding at least substantially specifically to epithelial cells is obtained as a result of conventional hybridoma formation, expression, and screening, or as a result of making antibody fragments using phage display libraries (Huse et al., Science 246:1275, 1989; Clackson et al., Nature 352:624–628, 1991; Soderlind et al., Immunilogical reviews 130:109, 1992). The monoclonal antibodies and receptors can be of any mammalian species, including murine, rabbit, human or the like. The antibodies can be of any class or subclass, such as IgA, IgD, IgG, IgM, and can include human subclasses IgGl, 2, 3, or 4, mouse IgG1, 2a, 2b, or 3, or the equivalents thereof in other species; see Roitt et al., "*Immunology*," (2nd ed., 1989), Ch. 5. In preferred embodiments, most or even all of the constant regions of the source antibody are deleted from the fusion construct; consequently the class and subclass of the source antibody are of little importance.

Methods for preparing monoclonal antibodies are well established as evidenced by numerous references in the scientific literature. An animal is hyperimmunized with a suitable immunogen, with or without addition of adjuvant. Various epithelial cells can be used as the immunogen, particularly human epithelial cells, including tumor cells originating from epithelial cells, for example ME180 cells. Cells from other species also can be used, e.g., primates. Whole cells are preferred, however homogenates, membrane fragments or the like, can be used. The source of the cells includes cells in tissue culture, biopsy specimens, and the like. Antibody-producing cells such as those from the spleen of the immunized animal, are removed and immortalized, typically by cell fusion with an immortal cell line, to produce a hybridoma. Alternative means of lymphocyte immortalization, such as transformation with an immortalizing virus, e.g. Epstein-Barr virus, are also possible. For convenience, all immortalized monoclonal antibody producing cells regardless of method of immortalization are referred to hereinafter as hybridomas.

To identify hybridomas producing monoclonal antibodies of interest, antibodies secreted by the immortalized cells, whether in culture or in ascites fluid, are screened to identify the clones that secrete antibodies of the desired characteristics. The most important characteristic of such antibodies is "substantially specific" binding to lens epithelial cells, i.e., the ability of the antibody to bind to lens epithelial cells at concentrations at which its binding to other structures within the posterior or anterior chambers of the eye is negligible. Preferably the amount of antibody bound per unit area to other cell types within the eye will be less than 5%, more preferably less than 2%, of the amount of antibody that is bound to lens epithelial cells. A second desirable characteristic of such antibodies is high affinity binding to the epithelial cell antigen. High affinity preferably means a dissociation constant ($K_d$) of $10^{-7}$M or less. Screening of the hybridoma clones can be performed by binding to epithelial cells, particularly lens epithelial cells, using an ELISA assay. Other screening methods include radioimmunoassay and immunohistochemical staining of cryostat sections of ocular tissue.

After a hybridoma producing a monoclonal antibody having appropriate specificity for epithelial cells is identified, cDNA encoding the antibody is isolated from the corresponding hybridoma. This is accomplished by preparing cDNA from messenger RNA (mRNA) obtained from hybridoma cells by conventional means, followed by ligation of the cDNA into phage λ to produce an expression library. The preferred vector is lambda ZAP II from Stratagene (La Jolla, Calif.), although other variants can be used. The ligation mixture is packaged by conventional means and used to transfect *E. coli*. The preferred strain of *E. coli* is XL1-Blue from Stratagene, although other strains can also be used, for example Y1090r- (*Molecular Cloning, A Laboratory Manual*, Sambrook, J., et al., Cold Spring Harbor Laboratory Press, Plainview, N.Y.). The infected bacteria are plated out on agar plates so that isolated plaques are observed.

Expression of light and heavy chain antibody genes is determined by immunoblot screening of the plaques. The preferred antibodies used to screen the λ library bind to the constant regions of either the heavy or light chain of the mouse monoclonal antibody and are conjugated to alkaline phosphatase or peroxidase so that a color development reaction can be used to detect the plaques to which they bind. Several plaques can be isolated to ensure that the heavy chain and light chain genes are represented. Those plaques which express antibody genes are purified by reinfection followed by screening, as described above, until a homogeneous preparation of phage is obtained from each of the original plaques.

The homogenous λ lysogen culture is coinfected with a helper phage, preferably M13KO7. The coinfected culture yields M13 transducing phage containing single stranded plasmid which harbors a gene encoding either $V_H$ or $V_L$.

The transducing phage containing lysate is isolated by conventional methods and used to reinfect a culture of XL1-Blue. These cultures are used to stably maintain the cloned genes encoding the heavy and light chain on a plasmid vector. These plasmids are isolated and sequenced to confirm the identity of the genes as described below.

The genes encoding the desired variable regions of the light and heavy chains can also be cloned using the polymerase chain reaction. Specific primers are used in conjunction with a preparation of cDNA isolated from the hybridoma to amplify a region of the cDNA that encodes the $V_H$ and $V_L$. These amplified DNA fragments are then cloned into plasmid vectors The structure of a typical IgG antibody is shown in schematic form in FIG. 3 with the variable regions of the heavy and light chains as indicated. The variable regions in turn contain alternating framework (FR) and complementarity-determining (CDR) regions. In each chain, four FRs bracket three CDRs. The CDRs provide the surfaces which interact directly with antigen, while the FRs position the CDRs adjacent to each other in proper tertiary conformation. CDRs have variable sequences for antibodies of different specificities, whereas the FRs are more conserved for a given antibody type and species.

Primers for PCR amplification of the heavy and light chain variable regions are chosen to bind to the 5' and 3' ends of the respective variable regions. Primers for the 3' ends of the sequence encoding the light chain and heavy chain variable regions ($V_L$ and $V_H$, respectively) are readily obtained from the sequences encoding adjacent light chain and heavy chain constant domains.

The 5' primers can be obtained in several ways. First, the heavy and light chain N-termini of a particular monoclonal antibody having the desired characteristics are partially sequenced for 6–10 amino acids, and a DNA primer is synthesized based upon the corresponding deduced nucleotide sequence(s). Alternatively, a primer is designed corresponding to relatively conserved leader sequences or first framework region ($FR_1$) sequences of the heavy and light chains characteristic of the hybridoma source species.

The appropriate sets of primers are used to amplify the cDNAs which encode the variable regions of the light and heavy chains (See Chaudhury (1989); Pluckthun, *Bio/Technology* (1991) 9:545; Larrick et al., *Bio/Technology* (1989) 7:934.) The amplified $V_L$ and $V_H$ DNA fragments are purified by conventional techniques such as agarose gel electrophoresis on low melting agarose and cloned into plasmid vectors.

Several copies, generally at least three independently isolated copies, of the variable region heavy and light chain encoding DNA fragments sequenced to ensure that the variable regions contain the expected three complementarity determining regions (CDR1, CDR2, and CDR3) bracketed by four framework regions (FR1, FR2, FR3, and FR4). The variable framework regions can be abbreviated or modified, including humanized. Isolated heavy or light chain variable domains have selective binding affinity for their target antigens even without the presence of the complementary chain. (See Ward, *Nature* (1989) 341:544.) Although $V_L$ and $V_H$ peptides are capable of binding independently to antigen and either could be used alone as the specificity domain, the combination of both creates a single chain specificity domain of greater affinity and selectivity and is preferred. Appropriate DNA sequences encoding the $V_L$ and $V_H$ are joined in-frame, preferably through a DNA sequence encoding a "linker" region comprising one or more peptide linkages, to make a DNA sequence encoding a single chain specificity domain. Necessarily the single polypeptide produced by expression of the above DNA coding region has its composite domains joined through peptide linkages or bonds. Specificity domains of this structure will correspond to the general formula:

$$V_H\text{'-Li-}V_L\text{'} \qquad (3)$$

where Li indicates the linker region and $V_L$' and $V_H$' indicate light and heavy chain variable domains, respectively; the primes indicate that the variable regions can be substantially modified from the sequence of the parent antibody, especially in the FRs.

Either $V_L$ or $V_H$ can provide the N-terminus of the epithelial cell specific antigen binding or "specificity" domain. The intervening linker region can be of arbitrary length and sequence, but should be of sufficient length to permit the $V_L$ and $V_H$ polypeptides to interact correctly and provide for an appropriate tertiary structure. The distance between the C-terminus of $V_L$ and the N terminus of $V_H$ has been reported to span 3.7 nm; see Whitlow and Filpula, "Single Chain $F_v$ Proteins and/or Fusion Proteins," in Methods: A Companion to Methods in Enzymology (1991). Linkers of 10–30 amino acid residues are preferred, with those of 14–25 amino acid residues being more preferable. Flexible linkers also are preferred;

these may be designed using small soluble amino acids such as alternating glycine and serine residues. At a few positions along the linker, charged residues also can be introduced to enhance water solubility of the linker, since the N-terminal and C-terminal ends of the variable regions to be linked in general are solvent accessible. See Chaudhury, supra; Sastry et al., *Proc. Natl. Acad. Sci. USA* (1989) 86:5728–5732.

The specificity domain is cloned into an expression vector to permit testing of the resulting polypeptide for binding affinity and specificity. Expression of functional specificity domains is accomplished from bacterial hosts such as *E. coli*, or from eukaryotic hosts including yeasts, insect cells, or mammalian cells. Naturally, an appropriate expression vector is matched to the anticipated host cells. An appropriate expression vector comprises a promoter capable of providing transcription in the host species, transcriptional and translational start sequences, optionally a signal sequence to provide for secretion, the $V_L$ and $V_H$ coding sequences joined by a linker region, and translation and transcription termination sequences. Optionally, DNA encoding portions of the heavy and light chain constant regions may be included at the 3' ends of the $V_L$ and/or $V_H$ coding regions. The resulting expression vector is used to transform the appropriate host cell and obtain expression of the specificity domain. The expressed epithelial cell binding or specificity domain polypeptides are then screened to identify clones exhibiting lens epithelial cell specific binding. Screening for the specificity domain polypeptides is performed essentially as described supra for monoclonal antibodies. It generally is performed by radioimmunoassay or by competition with parent monoclonal antibody binding in an ELISA assay.

The specificity domains of polypeptides of the present invention are not restricted to domain sequences which are identical to those of the source monoclonal antibodies. In particular, the term "specificity domain" of the present invention encompasses an epithelial cell binding domain which is homologous to the variable region of an antibody heavy or light chain.

Other toxic agents may also be used, such as bismuth non-diffusively linked to the monoclonal antibodies or receptors as described by Waldman, *J. Amer. Med. Assoc.*

Alternatively, liposomes may be linked to the monoclonal antibodies or receptors, where the liposomes contain various cytotoxic agents, such as methotrexate, 5-fluorouracil, any of the above toxins, or the like. See, for example, Szoka and Papahadjopoulos, *Proc. Natl. Acad. Sci. USA* (1978) 75:4194–4198 and Szoka et al., *Biochem. et Biophys. Acta.* (1980) 601:559–571 for the preparation of liposomes, which disclosures are incorporated herein by reference. Linking of antibodies to the liposomes has been amply described in the literature, see for example Heath et al., *Proc. Natl. Acad. Sci. USA* (1983) 80:1377–1381 and Leserman et al., *Nature* (1981) 293:226–228, which disclosures are incorporated herein by reference.

Other cytotoxic agents conjugated to the binding moiety may also be employed in conjunction with the process of this invention. The cytotoxic agent can be used with other agents such as lysomotropic amines, carboxylic ionophores and calmodulin inhibitors. Examples include ammonium chloride, methylamine, chloroquine, monensin or verapamil. For descriptions of these agents, see, for example, Casellas et al., *Immunotoxin* (1988) Kluwer Academic Publishers; Myers et al., *Blood* (1984) 63:1178–1184; Casellas, *J. Biol. Chem.* (1984) 259:9359–9364; and Akiyama, *J. Cell Physiol.* (1984) 120:271–279.

The intraocular device comprising the polymer and the cytotoxic agent may be used in vivo, by introduction directly into the posterior chamber of the eye so as to provide for a higher concentration of the immunotoxin in the immediate vicinity of the posterior chamber and the lens capsule and remnant lens epithelial cells than in surrounding structures. The amount of the immunotoxin released from the intraocular device in a given period of time can be varied, depending upon the total amount of cytotoxic agent associated with the intraocular device and by the composition of the polymer, for example, the concentration of polymer, the viscosity, and the like.

For example, to decrease the rate of release, the polymer may be cross-linked so that diffusion is controlled by the size of the cytotoxic agent, or the polymer may contain a slight charge, so that the attraction between the polymer and the cytotoxic agent is more than simple diffusion into the polymer but does not constitute covalent bonding to the polymer.

The amount of cytotoxic agent associated with the intraocular device is of an amount sufficient to kill at least substantially all of the remnant lens epithelial cells in the eye following release from the device. Generally a total amount of between 0.1 to 20 µg, more usually 0.5 to 10 µg, preferably 1.0 to 5 µg is associated with the intraocular device. The amount of release of immunotoxin from the intraocular device is usually from about 10–25% for the initial hour of release, and reaches a steady state of amount of release of about 10% to 20% per hour thereafter.

The intraocular device may comprise a single cytotoxic agent reversibly associated with a polymer or it may comprise more than one cytotoxic agent. Other cytotoxic agents and/or antiproliferative drugs which may be used include methotrexate and daunorubicin. See, for example, Shawler et al., *J. Biol. Resp. Mod.* (1988) 7:608–618; Dillman et al., *Cancer Res.* (1988) 48:6097–6102. To provide the necessary specificity of action, the cytotoxic agents are preferably bound to an antibody, generally a monoclonal antibody, capable of binding at least substantially specifically to epithelial cells.

The intraocular device can be prepared by combining the various components in a sterile environment. The polymer and the cytotoxic agent can be provided in a convenient form, usually in the form of a solution, although in some instances the polymer may be provided as a solid, which is then coated with the cytotoxic agent directly, or which is coated with a polymer/cytotoxic agent dispersion. Preferably, the intraocular device is provided with an IOL support, the intraocular device being coated onto the surface of the lens so as to provide for ease of introduction into the posterior chamber or lens capsule. The intraocular device either with or without an IOL support, should fit inside the lens capsule for fixation in the ciliary sulcus and/or other parts of the eye wall with or without sutures. The intraocular device could also be placed in the anterior chamber when there is no or little lens capsule left, so that the immunotoxin could diffuse into the posterior chamber.

When the polymer comprises collagen or a derivative thereof, the collagenous material will normally be provided as a uniform dispersion of collagen fibers in solution. The cytotoxic agent may then be added to the collagenous dispersion with agitation to ensure the uniform dispersion of the cytotoxic agent in the resulting mixture. The amount of cytotoxic agent associated with the polymer will be sufficient to substantially completely or completely kill all of the lens epithelial cells following release from the polymer. Other materials, as appropriate, may be added concomitantly or sequentially. After ensuring the uniform dispersion of the various components in the mixture, the mixture may be sterilized by any means which will not interfere with the biological activity of the antiproliferative or other agents and sealed in an appropriate container. Preferably, sterilization will be achieved by using aseptic techniques and aseptic conditions to admix already sterile components.

In addition to the major components, a number of minor components may also be included for a variety of purposes. These agents will for the most part impart properties which protect the stability of the composition, control the pH, or the like, such as stabilizers including sugars, wetting agents, etc. Illustrative agents include phosphate or acetate buffers, methyl or propylparaben, polyethylene glycols, etc. These agents generally will be present in less than about 2 weight percent of the total composition, usually less than about 1 weight percent, and individually may vary from about 0.001 weight percent to about 1 weight percent.

As already indicated, in some instances the immunotoxin will be encapsulated, particularly in liposomes. Liposomes are prepared from a variety of lamellar-forming lipids including phospholipids, e.g., phosphatidylcholine, phosphatidylethanolamine, etc., gangliosides, sphingomyelins, steroids, e.g., cholesterol, etc.

Where the cytotoxic agent is a combination of monoclonal antibody and complement (either endogenous and/or exogenous), the monoclonal antibody can be introduced as described above for the cytotoxic agent. If exogenous complement is to be used, it is introduced, generally after 30 to 60 mins., into the anterior chamber in an amount of from 25–200, more usually from about 50–150 $\mu$l which agent will be present in an amount sufficient to substantially completely or completely kill all of the lens epithelial cells. The complement is a standard complement. By complement is intended normal serum of men or other vertebrates which comprises about 9 major proteins which react with antigen-antibody complexes to cause damage to cell membranes, and including lysis. A complement is usually supplied as serum, for example, rabbit serum. A typical complement and its preparation useful in the present invention is described in Monoclonal Antibodies (1980), Printing Press, New York Eds. Kennett, et al. pp. 391–392 which publication is incorporated herein by reference. Alternatively, it is possible to use patient complement activity which may be obtained in sufficient concentration from aqueous humor during surgery. The complement is prepared in an appropriate dilution of rabbit serum in a physiologically acceptable medium containing $Mg^{2+}$ and $Ca^{2+}$.

Generally, the cytotoxic effect will be realized within a relatively short time after binding of the cytotoxic agent to the cells, generally 0.5–15 hrs, depending upon the concentration of cytotoxic agent used and the rate of release of the cytotoxic agent from the intraocular device. Binding itself will occur within a relatively short time, after the instillation of the intraocular device. Where the cytotoxic effect is realized by the combination of monoclonal antibody and complement, the cytolytic effect is realized within a relatively short time after the introduction of complement, usually in about 0.5 hr.–1.0 hr; lysis of the target cells can be used to evaluate the onset of the cytolytic effect.

The development of secondary cataract can take from a few months to several years. Clinically, a secondary cataract is determined by slit lamp microscopy presenting as the appearance of lens epithelial cells growing on the posterior lens capsule. The invention described herein would allow for the prolonged release of therapeutic concentrations of lens epithelial cell specific cytotoxic agents that would destroy these cells and hence prevent their proliferation. Thus, slit lamp microscopy can be used to determine that development of a secondary cataract has not occurred. In cases where a secondary cataract does occur, either subsequent to treatment with the intraocular device, or in the absence of treatment, the intraocular device may be introduced into the anterior or posterior chamber as previously described for use at the time of cataract surgery for removal of a primary cataract.

The IOL may be provided already treated with the polymer in a form ready for reaction with the immunotoxin or as an IOL or other support coated with polymer and immunotoxin. Alternatively, the components for preparing the intraocular device are provided as lyophilized powders for reconstitution, as concentrated solutions, or ready for use. The subject compositions can be provided as kits for use in one or more operations. The kits will include the polymer and the cytotoxic agent in separate containers, either as concentrates (including lyophilized compositions), which may be further diluted prior to use in an appropriate diluent for use in the eye or at the concentration of use, where the containers can include one or more dosages. Conveniently, single dosages may be provided in sterile vials, so that the physician may employ the vials directly, where the vials have the desired amount and concentration of agents. Thus, the kit may have a plurality of vials containing the polymer as well as the cytotoxic agent in appropriate proportional amounts. Where the containers contain the formulation for direct use, usually there will be no need for other reagents for use with the method, although optionally the kit may include separate containers of complement for use with the IOL.

The following examples are offered by way of illustration and not by way of limitation.

EXPERIMENTAL

Preparation of monoclonal antibodies capable of binding at least substantially with lens epithelial cells and methods for preparing immunotoxins are provided for example in U.S. Pat. No. 4,871,350 and references cited therein, which disclosures are hereby incorporated by reference. Monoclonal antibody-producing cell lines have been deposited with the ATCC Accession Number HB9747.

EXAMPLE 1

Effect of Polyoxypropylene-polyoxyethylene Block Polymer (Pluronic® F68) on Antibody Binding to ME180 Cells Monoclonal antibody 4197X at 2 mg/ml was mixed with F68 to obtain a final concentration of antibody of 1 mg/ml and 10, 5, 2, 1 and 0% F68. These solutions were incubated for 1 hr at 37° C. followed by 24 hrs at 4° C. Aliquots (100 $\mu$l) were removed after the 1 and 24 hr time points, and diluted to a final concentration of 10 $\mu$g/ml antibody in DMEM containing 10% FBS and a standard amount of $^{125}$I-4197X.

ME180 cells (human cervix epithelial obtained from the ATCC) were grown to confluence in 96-well plates. The diluted antibody (200 μl) was then added to the culture plates containing the ME180 cells and evaluated for its capacity to competitively inhibit the binding of $^{125}$I-4197X to the ME180 cells. The wells were incubated for 1 hr at 37° C. after which they were washed to remove unbound antibody. To determine cell-associated radioactivity, the cells were solubilized in 10% SDS (50 μl per well) and the soluble extract harvested with a cotton-tipped applicator stick which was then counted in a gamma counter. Binding was compared to the cell-associated radioactivity in the absence of competing antibody. Preincubation of antibody with F68 had little effect on its subsequent ability to bind to target cells.

EXAMPLE 2

Determination of Volume of F68 Solution Associated with an Intraocular Device (IOL)

Two solutions of F68 and $^{125}$I-4197X antibody were prepared. One preparation contained 4197X-RA immunotoxin at a concentration of 50 μg/ml. The second preparation contained an equivalent volume of buffer instead of immunotoxin. The radioactivity in 1.0 ul of the immunotoxin preparation was determined to be 13,501 cpm. IOLs were immersed in these solutions and excess liquid allowed to drain off. The radioactivity associated with one of the IOLs was 48,438 cpm. The volume of F68 immunotoxin mixture associated with the IOLs was calculated to be 3.6 μl.

EXAMPLE 3

Evaluation of Release and Cytotoxicity of Immunotoxin from Intraocular Device Coated onto an IOL The release of radioactividevfrom an intraocular device coated onto an IOL, to cell culture medium is shown in Table 1. Two solutions of F68, immunotoxin and $^{125}$I-antibody were prepared, as described above. One preparation contained immunotoxin at a final concentration of 50 ug/ml. The final concentration of F68 was 10%. The other preparation contained an equivalent volume of buffer instead of immunotoxin. IOLs (sterilized by autoclaving) were immersed into these solutions and excess liquid allowed to drain off. The IOLs were allowed to dry for 2 hours at room temperature (until tacky). The IOLs were then placed in cell culture wells (24 well plate) containing ME 180 cells (25% confluent) and 1.0 ml of cell culture media containing 10% fetal bovine serum. The cells were incubated (37° C., 5% $CO_2$) until control wells reached confluence. At various times during incubation, samples of culture supernatant (50 ul) were removed and counted for radioactivity. At the end of the incubation period, the wells were examined microscopically for cell viability. Photographs were taken of all wells for later verification of results.

Viable cells were present in all wells not containing immunotoxin. IOLs alone had no effect on cell growth. There was a marked lack of cell growth and cell viability in wells containing immunotoxin. At 0.175 ug immunotoxin/IOL in 1.0 ml of cell culture media and assuming all immunotoxin was released into the media the effective concentration would be 0.175 ug/ml. The $IC_{50}$ of immunotoxin alone for continuous exposure as used in this experiment is approximately 0.02 μg/ml.

TABLE 1

Release of $^{125}$I-4197X from Intraocular Device (Polymer = F68) Coated onto IOL Support

| Time[1] | Total Released Radioactivity (cpm/well) |
|---|---|
| 0 | 0 |
| 1 | 22,896 |
| 3 | 35,485 |
| 18 | 59,128 |
| 72 | 62,223 |

[1]Hours after introduction of IOL into cell culture.

EXAMPLE 4

Determination of Volume of F68 Solution and Amount of Immunotoxin Associated with a Intraocular Device after Drying Three solutions of F68, immunotoxin and $^{125}$I-immunotoxin ($^{125}$IT) were prepared. The radioactivity in a specified volume (cpm/10 ul) of each preparation was determined. The three preparations had a final concentration of 10% F68 and 0, 4 and 20 ug/ml of immunotoxin. The final concentration of $^{125}$I-immunotoxin was the same in all three solutions and determined to average 1,434 cpm/μl. The immunotoxin concentration of the labeled material was very low and did not significantly contribute to the overall immunotoxin concentration. IOLs were immersed (three times at 2 minute intervals) in these solutions and excess liquid allowed to drain off. The volume of F68 associated with the IOLs was determined by counting three of the IOLs in a gamma counter. The results were an average of 8,915 cpm ±1812 cpm/IOL. Using this number, it was calculated that IOLs immersed in 4 ug/ml immunotoxin had 0.025 ug of associated immunotoxin/IOL and IOLs immersed in 20 ug/ml immunotoxin had 0.124 ug of associated immunotoxin/IOL.

EXAMPLE 5

Effect of Immunotoxin Released from Intraocular Devices on Human Lens Epithelial Cells in Vitro The release of radioactivity from IOLs coated with the intraocular device to cell culture medium, is shown in Table 2 (below). Three solutions of F68, immunotoxin and $^{125}$I-antibody was prepared as described above. IOLs (sterilized by autoclaving) were immersed into this solution and excess liquid allowed to drain off. The IOLs were allowed to dry for 18 hours until dry. The IOLs were placed in cell culture wells (24 well plate) containing HLE cells (from cataract surgery capsule explants and maintained under tissue culture conditions) in 1.5 ml of cell culture medium. The cells were incubated for 7 days. At various times (15 min., 60 min. and 24 hrs.), samples of culture supernatant (50 ul) was removed and counted. At the end of the incubation period, wells were examined microscopically for cell viability. Photographs were taken of all wells. At the end of the observation period IOLs were removed, rinsed once in PBS, and counted. As indicated in Example 4, the initial average IOL-associated cpm was 8,915±1,812. Following incubation in cell culture medium, the average cpm associated with the IOL was 153 cpm which corresponds to a release of 98.3% of the radioactivity associated with the intraocular device.

Viable human lens cells were present in all wells not containing immunotoxin. IOLs alone had no effect on cell growth. There was a marked lack of cell growth and cell viability in wells containing immunotoxin. Cells exposed to IOLs coated with immunotoxin at 4 ug/ml (0.025 µg/IOL) were partially affected. No viable cells were present in wells containing IOLs coated with immunotoxin at 20 ug/ml (0.124 µg/IOL).

TABLE 2

Release of $^{125}$I-4197X-RA from Intraocular Device (polymer = F68) Coated onto an IOL into Culture Supernatant

| Time | Mean Total Released Radioactivity[1,2]/Well | |
|---|---|---|
| | in cpm | % Initial IOL associated radioactivity |
| 15 minutes | 3,360 | 38 |
| 60 minutes | 4,590 | 51 |
| 24 hours | 10,890 | 122 |

[1]Control = 297 cpm/IOL
[2]Initial IOL-associated radioactivity before being placed into cell culture = 8,915 ± 1,812 cpm/IOL

EXAMPLE 6

Examination of Various Polymers for Coating IOLs with Immunotoxin

Plastic culture wells were used to simulate coating of IOLs. Immunotoxin (4197X-RA) was mixed with various polymers (See Table 3) and examined for cytotoxic activity following drying on to the plastic tissue culture wells. The simulated IOLs were prepared as follows. Polymer stock solutions were prepared in phosphate buffered saline (PBS) and sterilized by autoclaving. Equal portions of polymer and sterile immunotoxin (at 770 ug/ml) or polymer and PBS were mixed under sterile conditions and 20 ul of each of the resulting mixtures added to individual wells of a 24 well cell culture dish. The solutions were allowed to dry in a sterile hood with lids open at room temperature for 3 hours.

1.0 ml of cell culture media (M199 containing 10% fetal bovine serum) was added to simulated IOL to rehydrate the immunotoxin followed by gentle agitation for 30 minutes at room temperature. Following rehydration individual supernatants developed from simulated IOLs were assayed for cytotoxic activity against ME 180 cells using MTT Mosmann, J. Immunol. Methods (1983) 65:65 to measure the amount of cell proliferation. Immunotoxin diluted in PBS alone or in polymer without drying was also evaluated using the method described above. The effects on cell proliferation (expressed as percent inhibition of cell growth) for a simulated IOL containing about 0.24 ug/ml immunotoxin are shown in Table 3.

The simulated IOLs were prepared by combining immunotoxins with any of a variety of polymers and then drying them onto tissue culture plates for three hours, as described above. The majority of immunotoxin polymer mixtures were as active as untreated immunotoxin in PBS in inhibiting cell proliferation. Hydroxypropylmethylcellulose and polyvinylpyrrolidone were slightly more active; these polymers alone exhibited some antiproliferative activity (percent inhibition of cell growth 17.3 and 21.6 for the two polymers, respectively). All other polymers alone had little or no antiproliferative activity. Immunotoxin mixed with Pluronic F127 and Pluronic F68 antiproliferative lost activity as a result of drying. Immunotoxin in these polymers without drying gave percent inhibitions of 87.8 and 91.1 respectively. Immunotoxin in all other polymers without drying had essentially the same activity as immunotoxin in PBS.

TABLE 3

| Polymer[1] | Percent Inhibition of Cell Growth Immunotoxin 4197X-RA in Polymer (dried 3 hours)[2] |
|---|---|
| Methylcellulose (medium viscosity) 2% (Sigma Chemical Company) | 84 |
| Carboxymethylcellulose (medium viscosity) 2% (Sigma Chemical Company) | 83.1 |
| Hydroxpropylmethylcellulose (low viscosity) 2% (Sigma Chemical Company) | 88.7 |
| Hydroxpropylmethylcellulose (high viscosity) 2% (Sigma Chemical Company) | 100 |
| Polyvinylpyrrolidone (PVP-360) 5% (Sigma Chemical Company) | 100 |
| Polyethylene Glycol 40% (Sigma Chemical Company) | 76.2 |
| Pluronic F127 20% BASF Corporation | 42.8 |
| Pluronic F68 20% BASF Corporation | 43.9 |
| Methocel E4M 1% Dow Chemical Company | 86.7 |
| Methocel E50LV 2% Dow Chemical Company | 85.9 |
| Methocel E5 5% Dow Chemical Company | 82.6 |
| Methocel E15LV 5% Dow Chemical Company | 82.0 |
| Polyvinyl alcohol 5% Aldrich Chemical Corp. | 78.8 |

[1]The indicated % is the concentration of the polymer stock solution in PBS.
[2]4197X-RA in PBS Control (not dried) resulted in 86.8% inhibition of cell growth.

EXAMPLE 7

Release of 4197X-RA Immunotoxin from Intraocular Device Coated Onto a Simulated IOL and Cytotoxicity Polystyrene balls were used to simulate IOLs for this study. The immunotoxin used in these experiments was 4197X-RA. One part of immunotoxin was mixed with two parts Methocel E4M (1% in PBS) and one part maltose (1M). The release of radioactivity from immunotoxin-polymer coated polystyrene balls (¼ inch diameters Polysciences) over time is shown in Table 4. The release of cytotoxic activity from coated balls is shown in Table 5. Preparation of materials used in these experiments was performed with sterile reagents under sterile conditions.

In the experiment to determine rate of release of radioactivity from the simulated IOLs, the 4197X-RA was labeled with $^{125}$iodine. Individual balls were dipped into the coating mixture and allowed to air dry for two hours at room temperature. The coated balls were then dipped into a 5% solution of Methocel E15LV and allowed to air dry for 2 hours. This step was repeated two more times. After the final dip in Methocel E15LV the coated balls were allowed to air dry at room temperature overnight. Individual immunotoxin coated balls were then immersed into 1 ml of PBS (for determination of radioactive release) or M199 containing 10% FBS (for determination of cytotoxic activity release). At specified times balls (3 per time period for radioactivity, 2 per period for cytotoxity) were removed from incubation solutions. Ball-associated radioactivity was determined by placing the balls in a gamma counter.

TABLE 4

Release of $^{125}$-I-4197X-RA from Intraocular Device (Polymer = Methocel E4M) Coated Onto A Simulated IOL Support

| Time (Minutes) | Percent Released Radioactivity[1] |
|---|---|
| 10 | 7.9 |
| 20 | 17.9 |
| 30 | 21.6 |
| 60 | 46.7 |
| 120 | 70.2 |

[1]Values are the mean of 3 determinations using 3 balls per time point.

cytotoxic activity associated with the incubation solution was determined by titration of the solution and exposing the dilutions to ME 180 cells. An MTT assay was used to determine the percent inhibition of cellular proliferation.

TABLE 5

Release Of 4197X-RA Cytotoxicity From Intraocular Device (Polymer = Methocel E4M) Coated Onto A Simulated IOL Support

| Time (Minutes) | Percent Cytotoxic Activity Released[1] |
|---|---|
| 10 | 3 |
| 20 | 25 |
| 30 | 42 |
| 60 | 50 |
| 120 | 100 |

[1]Values are the mean of 2 determinations using 2 balls per time point.

EXAMPLE 8

Evaluation of Cytotoxicity of 3D4-RA Immunotoxin Intraocular Device Coated Onto an IOL Over Time The release of cytotoxic activity of an immunotoxin (3D4-RA) from an intraocular device coated onto an IOL was evaluated. The following steps were performed with sterile reagents under sterile conditions. Immunotoxin 3D4-RA (1.56 mg/ml) was mixed with Methocel E4M and maltose as described in Example 7. Four polymethylmethacrylate (PMMA) intraocular lenses (Alcon) were dipped into the mixture. Two of the IOLs were allowed to dry and coated with Methocel E15LV as in Example 7 and the remaining two were immediately placed in 1 ml M199 containing 10% FBS and incubated for 6 hours at 4° C. After 24 hours the coated and dried IOLs were placed in M199 and incubated for 6 hours at 4° C.?. Cytotoxic activity of the extracts was analyzed on ME 180 cells using MTT to determine inhibition of cellular proliferation as described in Examples 6 and 7. The cytotoxic activity extracted from IOLs coated with 3D4-RA in polymer and dried for 24 hours was the same as that extracted from IOLs coated but not dried (control).

EXAMPLE 9

In Vivo Analysis of 3D4-RA Immunotoxin[1] Intraocular Device Coated IOLs for the Prevention of Secondary Cataract Immunotoxin associated with an IOL would place the cytotoxic agent in immediate proximity with the target cell population and increase residence time of the immunotoxin and the cytotoxic agent in the eye. These factors could lead to a more efficacious killing of target lens epithelial cells. Secondary cataract typically develops in rabbits within a few weeks following cataract surgery as indicated by proliferation of residual lens epithelial cells on the posterior lens capsule. The effect of IOLs coated with a 3D4-RA immunotoxin intraocular device on proliferation of residual lens cells was evaluated in vivo in a rabbit model. In this study, a 3D4-RA immunotoxin device-coated IOL was used.

4197X does not bind rabbit lens epithelial cells, an immunotoxin was constructed using a different monoclonal antibody, 3D4. This antibody, while being less specific than 4197X, does bind rabbit lens epithelial cells and kills these cells in vitro when coupled to ricin A.

Four normal female white New Zealand rabbits were randomly assigned to two treatment groups: (1) control group, and (2) immunotoxin treatment group. Both groups underwent lens extraction surgery with phacoemulsification in one eye. The surgical procedure simulated the method used on humans to remove primary cataracts. Group 1 received untreated lenses, group 2 received lenses treated with a polymer coating containing immunotoxin as described in Example 8.

All of the rabbits received one week of standard post-surgical care involving anti-inflammatory (topical steroid and antibiotic (topical gentamicin) treatment. The animals were observed for four weeks after surgery. At four weeks all animals were sacrificed and their eyes were collected. None of the animals exhibited gross toxicological or pathological reactivities to the implanted lenses.

Eyes were processed for histology, embedded into parafin and cut into thin sections, individual sections were stained and examined microscopically. The microscopic evaluation of the explanted eye sections revealed that the control eyes containing the untreated lenses exhibited epithelial cell growth on anterior and posterior walls of the lens capsule, i.e., development of secondary cataract. Deeper sections showed substantial epithelial cell piling on the anterior wall with a single layer of epithelial cells present on the posterior capsule wall with additional piling of cells at the equatorial regions.

The examination of sections from eyes containing the immunotoxin-treated lenses revealed little or no cellular growth on the lens capsule except in the extreme equatorial regions. Epithelial cell piling on the anterior capsule and epithelial growth on the posterior capsule were decreased absent. The decreased amount of epithelial cell growth in the immunotoxin-treated eyes was considered significant. No evidence of toxicity in the iris, choroid, or retina segments of the eye, was noted in any lens type.

These preliminary results, even though conducted with a small group of animals, are significant in that they suggest (1) that an immunotoxin having the capacity to bind to lens epithelial cells can prevent development of secondary cataract, and (2) it is possible to deliver imnunotoxin in a polymeric carrier via an IOL.

Coating IOLs with intraocular devices comprising solutions of immunotoxin in 10% F68 provides a mechanism to deliver immunotoxin in association with the IOL. Active (as determined by its ability to kill target cells) immunotoxin is released into the IOL environment over time. All of the IOL-associated immunotoxin is released from the IOL within 24 hours.

By implanting the subject intraocular device into the anterior chamber, remnant lens epithelial cells can be prevented from proliferating, thus avoiding secondary cataracts. The use of an intraocular device either as a stand alone device or with an IOL support provides a superior means for delivery of immunotoxin by allowing for release of immunotoxin over time and protection of the immunotoxin from degradative processes in the eye. The subject methods and device provide a simple procedure for preventing secondary cataracts.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. An intraocular device comprising:
    a biologically inert polymer linked to an immunotoxin conjugate, said immunotoxin conjugate comprising a toxic agent and an antibody, wherein said antibody moiety is capable of binding at least substantially specifically to epithelial cells, and wherein said immunotoxin conjugate is associated reversibly with said polymer so as to provide for sustained delivery of said immunotoxin conjugate following implantation of said device into an eye.

2. The device according to claim 1, wherein said antibody is a monoclonal antibody.

3. The device according to claim 2, wherein said toxic agent is a ricin A-chain.

4. The device according to claim 1, wherein said intraocular device is coated onto a surface of an intraocular lens or an "O" ring of a form suitable for use with an intraocular lens.

5. The device according to claim 4, wherein said "O" ring is degradable in said eye.

6. The device according to claim 1, wherein said polymer is water insoluble.

7. The device according to claim 6, wherein said polymer is hydrated.

8. The device according to claim 7, wherein said polymer comprises a hydrogel.

9. The device according to claim 8, wherein said hydrogel comprises a cross-linked matrix.

10. A method for preventing secondary cataracts which form following extracapsular extraction, said method comprising:
    implanting, during or immediately after extracapsular extraction, an intraocular device into the anterior or posterior chamber of the eye, wherein said intraocular device comprises a biologically inert polymer noncovalently linked to an immunotoxin conjugate comprising a toxic agent and an antibody, wherein said antibody is capable of binding at least substantially specifically to epithelial cells, and wherein said immunotoxin conjugate is associated reversibly with said polymer and when released from said polymer is present in the anterior chamber for a time and in an amount sufficient to kill at least substantially all residual lens epithelial cells.

11. A method for preparing an intraocular device, said method comprising:
    contacting a biologically inert polymer with an immunotoxin conjugate to form a noncovalent linkage, said immunotoxin conjugate comprising a toxic agent and an antibody, wherein said antibody is capable of binding at least substantially specifically to epithelial cells, so that said immunotoxin conjugate is associated reversibly with said polymer.

12. The method according to claim 11, wherein said noncovalent linkage is entrapment of said immunotoxin conjugate within said polymer or adsorption of said immunotoxin conjugate to said polymer.

* * * * *